(12) United States Patent
Macpherson et al.

(10) Patent No.: US 9,116,882 B1
(45) Date of Patent: Aug. 25, 2015

(54) IDENTIFICATION OF MATRILINEAL OR PATRILINEAL RELATIVES

(71) Applicant: 23andMe, Inc., Mountain View, CA (US)

(72) Inventors: John Michael Macpherson, Mountain View, CA (US); Michael Polcari, San Francisco, CA (US); Brian Thomas Naughton, Mountain View, CA (US)

(73) Assignee: 23andMe, Inc., Mountain View, CA (US)

( * ) Notice: Subject to any disclaimer, the term of this patent is extended or adjusted under 35 U.S.C. 154(b) by 132 days.

(21) Appl. No.: 13/804,178

(22) Filed: Mar. 14, 2013

Related U.S. Application Data

(60) Provisional application No. 61/678,912, filed on Aug. 2, 2012.

(51) Int. Cl.
*G06F 19/24* (2011.01)
*G06F 19/28* (2011.01)

(52) U.S. Cl.
CPC ............... *G06F 19/28* (2013.01); *G06F 19/24* (2013.01)

(58) Field of Classification Search
CPC ................................ G06F 19/24; G06F 19/28
See application file for complete search history.

(56) References Cited

U.S. PATENT DOCUMENTS

| | | | |
|---|---|---|---|
| 2003/0172065 A1* | 9/2003 | Sorenson et al. | 707/6 |
| 2008/0154566 A1* | 6/2008 | Myres et al. | 703/11 |
| 2010/0199222 A1* | 8/2010 | Kranik et al. | 715/853 |
| 2010/0287213 A1* | 11/2010 | Rolls et al. | 707/803 |

* cited by examiner

*Primary Examiner* — William Spieler
(74) *Attorney, Agent, or Firm* — Van Pelt, Yi & James LLP

(57) ABSTRACT

Determining relative relationships among a plurality of individuals, comprising: accessing user-specified genealogical information of at least some of the plurality of individuals and genetic information of recombinable deoxyribonucleic acids (DNAs) of at least some of the plurality of individuals; determining, using one or more computer processors and among the plurality of individuals, one or more related individuals who are relatives of a target individual, and information pertaining to the one or more related individuals, and presenting information pertaining to at least one of the one or more related individuals, including to present an indication of whether the at least one of the one or more related individuals is a matrilineal relative or a patrilineal relative of the target individual.

23 Claims, 22 Drawing Sheets

| Ancestry Information | | | Who Can See This |
|---|---|---|---|
| ✽ Ancestry | Eastern Asia ▸ | | all 23andMe members ▸ |
| Birthplace | United States ▸ | 94043 | all 23andMe members ▸ |
| Family Surnames | Lim; Oh; Chen; Heng | 19/3000 | all 23andMe members ▸ |
| Family Locations | United States; China; Singapore; United Kingdom | 47/3000 | all 23andMe members ▸ |
| About My Family | Write a little bit about your family history | 0/3000 | all 23andMe members ▸ |

Activity Settings

☑ Show my badges in my community posts and in my Public Profile. (Regardless of your selection, your badges may appear on pages only you can see, such as 23andWe Discovery reports and your own news feed.)

FIG. 2A relative finder

| SEARCH MEMBERS | SORT BY RELATIONSHIP ⬍ | 25 PER PAGE ⬍ | | | LIST VIEW ⌖ MAP VIEW ⇌ SURNAME VIEW |
|---|---|---|---|---|---|
| | | | | | <<< 1-25 OF 56 >>> |
| ☒ DANA LIM FEMALE * **** | | YOU | | | UPDATE YOUR PROFILE |
| ☒ FRANK LIM MALE * **** | | FATHER *************** | UNITED STATES UNITED KINGDOM CHINA, SINGAPORE, USA EASTERN ASIA LIM CHEW HENG 2 MORE D4K | A4 | OWNED PROFILE |
| ☒ MOLLY LIM FEMALE | 506 | MOTHER *************** | SINGAPORE SOUTH ASIA LIM HENG CHEW LOH ***** | CHEW | SHARING GENOMES SEND A MESSAGE |
| ☒ JOHN LIM MALE 508 | | BROTHER *************** | SINGAPORE SINGAPORE CHEW D4K ****** | | SHARING GENOMES SEND A MESSAGE |
| ☒ FEMALE | | 3RD TO 6TH COUSIN *************** | ** | | INTRODUCTION SENT VIEW CANCEL |
| ☒ MALE 502 | | 3RD TO 6TH COUSIN *************** | ***** CENTRAL ASIA M761 ***** | | INTRODUCTION SENT VIEW CANCEL |
| ☒ MALE 510 | | 3RD TO DISTANT COUSIN *************** | **** | | INTRODUCTION SENT VIEW CANCEL |
| ☒ DOUG YEE MALE | 504 | 3RD TO DISTANT COUSIN *************** | EASTERN ASIA PO **** LAO 9 MORE ***** M9A | | INTRODUCTION ACCEPTED VIEW CONVERSATION |
| ☒ FEMALE | | 3RD TO DISTANT COUSIN *************** | G1C | | INTRODUCTION SENT VIEW CANCEL |
| ☒ MALE | | 3RD TO DISTANT COUSIN *************** | G1C ****** | | SEND AN INTRODUCTION |
| ☒ EMILY HSU FEMALE, **** | | 3RD TO DISTANT COUSIN *************** | G1C | | PUBLIC MATCH SEND A MESSAGE |
| ☒ FEMALE | | 3RD TO DISTANT COUSIN *************** | CHINA MALAYSIA EASTERN ASIA ***** | | SEND AN INTRODUCTION |
| ☒ SAM PENG MALE * ***** | | 3RD TO DISTANT COUSIN *************** | ***** | | INTRODUCTION ACCEPTED VIEW CONVERSATION |

FIG. 5

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| MAKE CONTACT | 4TH COUSIN | 4TH TO 10TH COUSIN | FEMALE MATERNAL HAPLOGROUP F3 | 0.19% | 2 |
| MAKE CONTACT | 5TH COUSIN | 3RD TO 10TH COUSIN | FEMALE CENTRAL ASIAN ANCESTRY MATERNAL HAPLOGROUP G | 0.12% | 1 |
| MAKE CONTACT | 5TH COUSIN | 3RD TO 10TH COUSIN | MALE MATERNAL HAPLOGROUP G1A PATERNAL HAPLOGROUP B1b1b2a1a2d | 0.11% | 1 |
| MAKE CONTACT | 5TH COUSIN | 4TH TO 10TH COUSIN | MALE MATERNAL HAPLOGROUP R9b PATERNAL HAPLOGROUP O3a3c | 0.10% | 1 |
| MAKE CONTACT | 5TH COUSIN | 4TH TO 10TH COUSIN | FEMALE MATERNAL HAPLOGROUP B | 0.09% | 1 |
| MAKE CONTACT | 5TH COUSIN | 4TH TO 10TH COUSIN | MALE MATERNAL HAPLOGROUP D4C1 PATERNAL HAPLOGROUP O3a | 0.09% | 1 |
| MAKE CONTACT | 5TH COUSIN | 4TH TO 10TH COUSIN | MALE MATERNAL HAPLOGROUP F1a1* PATERNAL HAPLOGROUP O1a1* | 0.09% | 1 |
| SHARING GENOMES SEND A MESSAGE | PARENT OR CHILD | - | ****** MATERNAL HAPLOGROUP C | 50.11% | 24 |

FIG. 10C

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| THIS PERSON WOULD LIKE TO CONTACT YOU. VIEW MESSAGE | AUNT/UNCLE NEPHEW, NIECE OR HALF-SLIBLING | - | DANIEL LAWRENCE RF2_, MATERNAL HAPLOGROUP U5a1* PATERNAL HAPLOGROUP R1b1b2a1a2d3* | 20.22% | 43 |
| CONTACT ACCEPTED SEND A MESSAGE VIEW CONVERSATION | SIBLING | - | ERIN LAWRENCE RF2_, MATERNAL HAPLOGROUP H1 | 46.75% | 29 |

FIG. 10G

| | | | | | |
|---|---|---|---|---|---|
| Dana | A G T | C T G | C A A | ... | -- 1502 |
| | C G A | C A G | T C A | ... | -- 1504 |
| Bob | C A T | G A C | C C G | ... | -- 1506 |
| | A A T | C T G | C A A | ... | -- 1508 |

FIG. 15

IDENTIFICATION OF MATRILINEAL OR PATRILINEAL RELATIVES

CROSS REFERENCE TO OTHER APPLICATIONS

This application claims priority to U.S. Provisional Patent Application No. 61/678,912 entitled IDENTIFICATION OF MATRILINEAL OR PATRILINEAL RELATIVES filed Aug. 2, 2012 which is incorporated herein by reference for all purposes.

BACKGROUND

Genealogy is the study of the history of families and the line of descent from ancestors. It is an interesting subject studied by many professionals as well as hobbyists. Traditional genealogical study techniques typically involve constructing family trees based on surnames and historical records. As gene sequencing technology becomes more accessible, there has been growing interest in genetic ancestry testing in recent years.

Existing genetic ancestry testing techniques are typically based on deoxyribonucleic acid (DNA) information of the Y chromosome (Y-DNA) or DNA information of the mitochondria (mtDNA). Aside from a small amount of mutation, the Y-DNA is passed down unchanged from father to son and therefore is useful for testing patrilineal ancestry of a man. The mtDNA is passed down mostly unchanged from mother to children and therefore is useful for testing a person's matrilineal ancestry. These techniques are found to be effective for identifying individuals that are related many generations ago (e.g., 10 generations or more), but are typically less effective for identifying closer relationships.

Genealogy researchers are often interested in learning whether a relative of a person is a patrilineal relative (i.e., a relative on the person's father's side) or a matrilineal relative (i.e., a relative on the person's mother's side). Existing personal genetics services, however, typically do not provide such information since the information can be difficult to ascertain on the basis of just the genetic information of the person and the relative.

BRIEF DESCRIPTION OF THE DRAWINGS

Various embodiments of the invention are disclosed in the following detailed description and the accompanying drawings.

FIGS. 2A-2B are example user interface screens illustrating various configuration options.

FIG. 5 is an example user interface screen of an embodiment of a list view interface displaying the relatives found in a process such as 300.

FIGS. 10A-10H are screenshots illustrating user interface examples in connection with process 1300.

FIG. 15 is a diagram illustrating an example in which phased data is compared to identify IBD.

DETAILED DESCRIPTION

Figure 1:
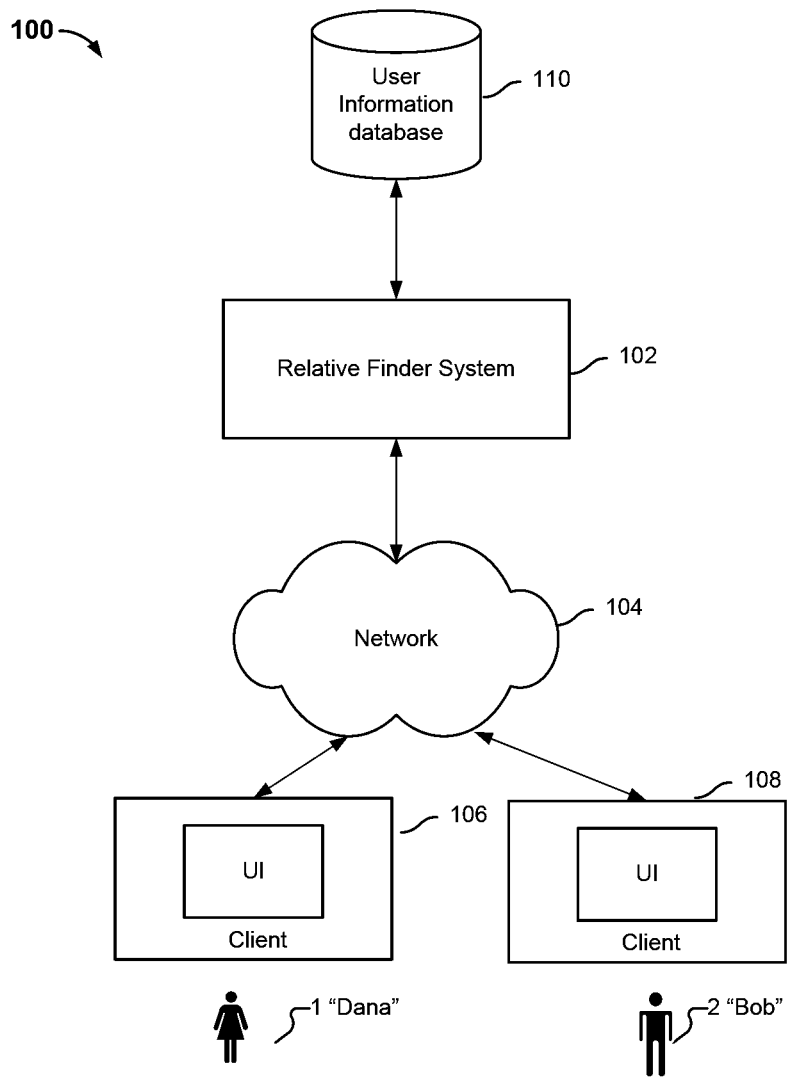
FIG. 1 is a block diagram illustrating an embodiment of a relative finding system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Finding among a number of individuals patrilineal or matrilineal relatives (also referred to as paternal or maternal relatives) of a target individual is described. As used herein, a relative of a target user refers to anyone who has at least one common ancestor with the target user within N generations (where N is a configurable number, in some cases set to 5 or 6 but is adjustable according to the requirements of the system or as specified by a user). The technique combines user-specified genealogical information (e.g., family trees) and genetic information (e.g., information on genetic markers such as Single Nucleotide Polymorphisms (SNPs), Short Tandem Repeats (STRs), and Copy-Number Variants (CNVs), and/or genome sequence information, etc.) to identify relatives of a target individual. In some embodiments, the identifications of matrilineal relatives is made based at least in part on matching the genetic information of a number of individuals with the genetic information of a known matrilineal relative of the target individual (preferably a close matrilineal relative such as mother, a maternal aunt or uncle, or a maternal grandparent). Similarly, in some embodiments, the identifications of patrilineal relatives is made based at least in part on matching the genetic information of the individuals with the genetic information of a known patrilineal relative of the target individual (e.g., father, a paternal aunt or uncle, or a paternal grandparent). Techniques such as identification of "Identical by Descent" (IBD) regions are used in some embodiments to make the identification. Information about the identified relatives is presented to the target individual, including an indication of whether an identified relative is a matrilineal relative or a patrilineal relative of the target individual.

In various embodiments, the results are displayed in a list view, a map view, according to surnames, or in many other appropriate ways. In some embodiments, the user is given the options to view matrilineal relatives separately from patrilineal relatives, or to view the relatives in a combined view where matrilineal relatives and patrilineal relatives are annotated differently. For example, separate lists of matrilineal relatives and patrilineal relatives can be displayed, or a combined list can be displayed in which matrilineal relatives and patrilineal relatives are shown differently; the geographical locations of the matrilineal relatives can be displayed separately from those of the patrilineal relatives, or the locations can be displayed together but the matrilineal relatives are represented differently from the patrilineal relatives; surnames associated with matrilineal relatives are displayed separately from surnames associated with patrilineal relatives, or the two types of surnames can be displayed together but indicated differently. Other techniques of displaying matrilineal and patrilineal relatives in ways that are easily discernible by the user can be employed.

Because of recombination and independent assortment of chromosomes, the autosomal DNA and X chromosome DNA (collectively referred to as recombinable DNA) from the parents is shuffled at the next generation, with small amounts of mutation. Thus, only relatives will share long stretches of genome regions where their recombinable DNA is completely or nearly identical. Such regions are referred to as "Identical by Descent" (IBD) regions because they arose from the same DNA sequences in an earlier generation. Locating IBD regions in the recombinable chromosomes of individuals allows related individuals to be identified.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same or at least compatible indicate that the rest of the sequences, although not assayed directly, are also likely identical.

FIG. 1 is a block diagram illustrating an embodiment of a relative finding system. In this example, relative finder system 102 may be implemented using one or more server computers having one or more processors, one or more special purpose computing appliances, or any other appropriate hardware, software, or combinations thereof. The operations of the relative finder system are described in greater detail below. In this example, various users of the system (e.g., user 1 ("Dana") and user 2 ("Bob")) access the relative finder system via a network 104 using client devices such as 106 and 108. User information (including personal information such as user-specified genealogical information (e.g., family information), population group, etc., and optionally genetic information) pertaining to the users is stored in a database 110, which can be implemented on an integral storage component of the relative finder system, an attached storage device, one or more separate storage devices accessible by the relative finder system, or a combination thereof. Many different arrangements of the physical components are possible in various embodiments. In various embodiments, the entire genome sequences and/or assayed DNA markers (e.g., SNPs, STRs, CNVs, etc.) are stored in the database to facilitate the relative finding process. For example, in some implementation, each user is provided with the option to purchase a sample collection kit to collect a DNA sample such as saliva, which is assayed to determine approximately 650,000 SNPs in the individual's genome. The assayed genetic data, if available, is stored in the database. In the examples below, using SNPs to find relatives in a database is discussed extensively for purposes of illustration; however, other types of markers, full genome sequences, or any other appropriate types of genetic information can be used. In some embodiments, the user is not required to provide the DNA sample or have genetic data stored in the database. As will be described in greater detail below, a user who is not genotyped or sequenced but has one or more close relatives (such as parents, aunts, uncles, or grandparents) whose genetic information is available in the database can still find relatives by relying on the genetic information of those close relatives. Various applications are provided for the user to access his/her data as well as make connections with other users in the system.

In some embodiments, the relative finder system provides, via the network and using the client software, user interfaces for a user to specify genealogical information such as information about the user's parents. Given the simple user input information, the system can make determinations of the user's paternal and/or matrilineal relatives. Additional genealogical information such as the user's aunts, uncles, and/or grandparents can be optionally entered. The information can be stored in the database.

System 100 shown in this example includes genetic and other additional non-genetic information for many users. By comparing the recombinable DNA information to identify IBD regions between various users, the relative finder system can identify users within the database that are relatives. In some embodiments, assuming that the target user's parents' genetic information is also available in the database, the recombinable DNA information of the target user's mother (or father) is compared with that of other users in the database to identify matrilineal (or patrilineal) relatives. Since more distant relationships (second cousins or further) are often unknown to the users themselves, the system allows the users to "opt-in" and receive notifications about the existence of relative relationships. In some embodiments, users are also presented with the option of connecting with their newly found relatives.

Figure 2B:
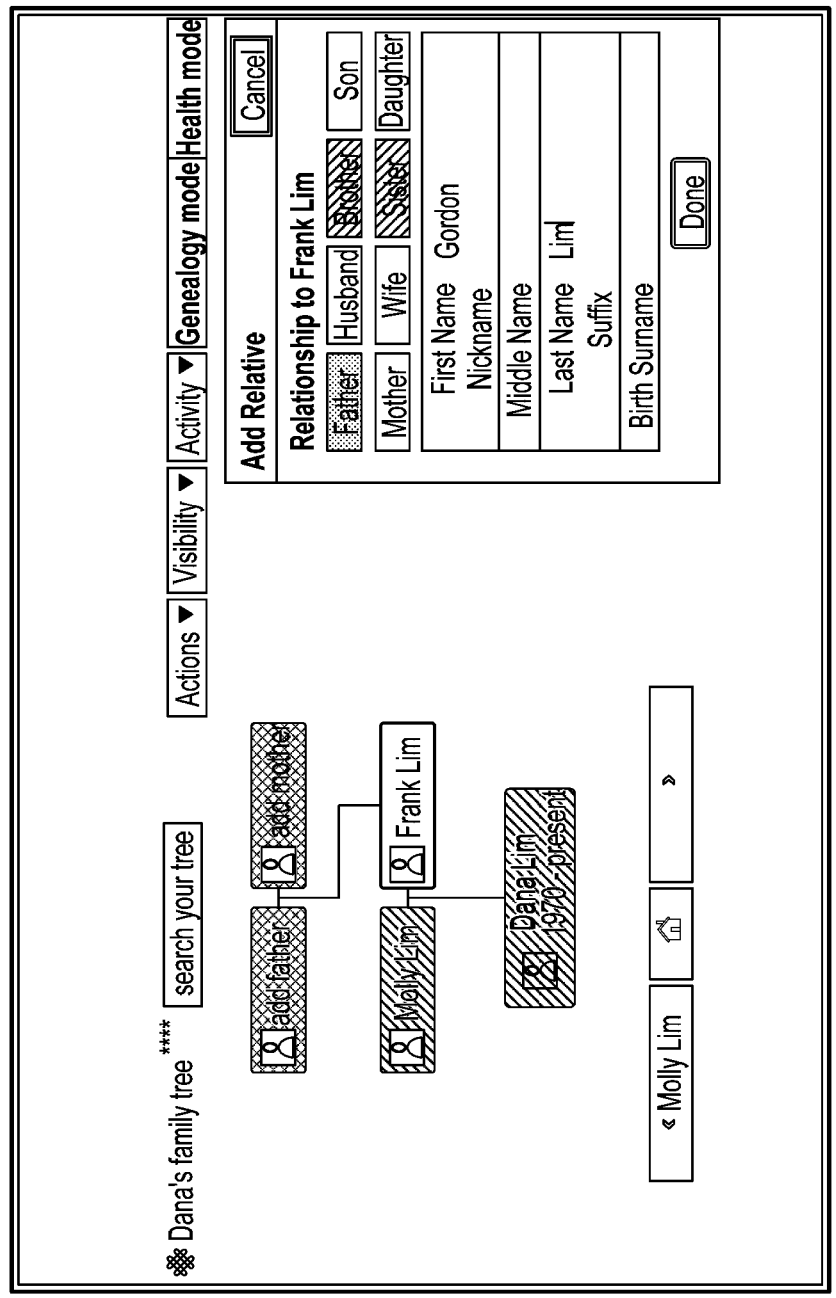

When a user joins system 100, she is provided with options to specify certain personal information. FIGS. 2A-2B are example user interface screens illustrating various configuration options.

First, the user is asked to enter various personal information. FIG. 2A is an example user interface screen illustrating some of the configuration options for a user's personal information. The user is asked about ancestry, birthplace, family surnames (e.g., surnames of close family members such as parents or grandparents), family locations (e.g., where the user has lived), etc. As will be described in greater detail below, the personal information is stored and can be used for different types of displays, such as displaying relatives according to surnames or family locations.

Next, the user is asked to enter genealogical information. FIG. 2B is an example user interface screen illustrating the specification of a family tree by a user. In this example, a target user named Dana Lim is presented with a user interface to establish a family tree. As shown, Dana is presented with a template to add information about close relatives who are useful for identifying additional matrilineal or patrilineal relatives in the database, specifically her father Frank Lim and her mother Molly Lim. She also has the option to add maternal or paternal grandparents, maternal or paternal uncles or aunts, etc., all of whom are useful in identifying additional matrilineal or patrilineal relatives. In this example, information about Dana's siblings is not used for matrilineal/patrilineal relative identification, since, like Dana, her siblings inherited genes from both parents, and the determination of which genes were inherited from which parent can be difficult unless the parents' genetic information is available. In some embodiments, the system lets the user enter additional information about her family members that should be accounted for during the relative finding process, such as whether a particular individual is adopted or has half siblings. For example, depending on an adopted individual's relationship to Dana, the individual may be discounted from the relative finding process (e.g., genetic information about an adopted maternal uncle is not used as the basis for finding more relatives), or the relatives of the relative may be discounted from the relative finding process (e.g., an adoptive parent means genetic information of the adoptive grandparents is not used as the basis for finding more relatives). For a half sibling, the non-shared parent is discounted from the relative finding process (e.g., if an individual's mother and a maternal uncle are by different fathers but the same mother, then the father of the maternal uncle is not used as the basis for finding additional relatives of the individual).

In this example, as soon as Dana enters a member in the family tree, the system searches for one or more candidate users in its database that have names or identifiers that match what Dana has entered, and presents the candidate users to Dana to confirm or select as appropriate. Once Dana confirms that, for example, a user named Frank Lim is indeed her father, she is presented with a request to give permission for the system to use Frank and Molly's data to look up relatives in the database. In some embodiments, each user is given the option to provide a one-time consent that others in the system can look up their data for relative finding purposes. In some embodiments, two users are required to connect to each other before they can view each other's information.

Figure 3:
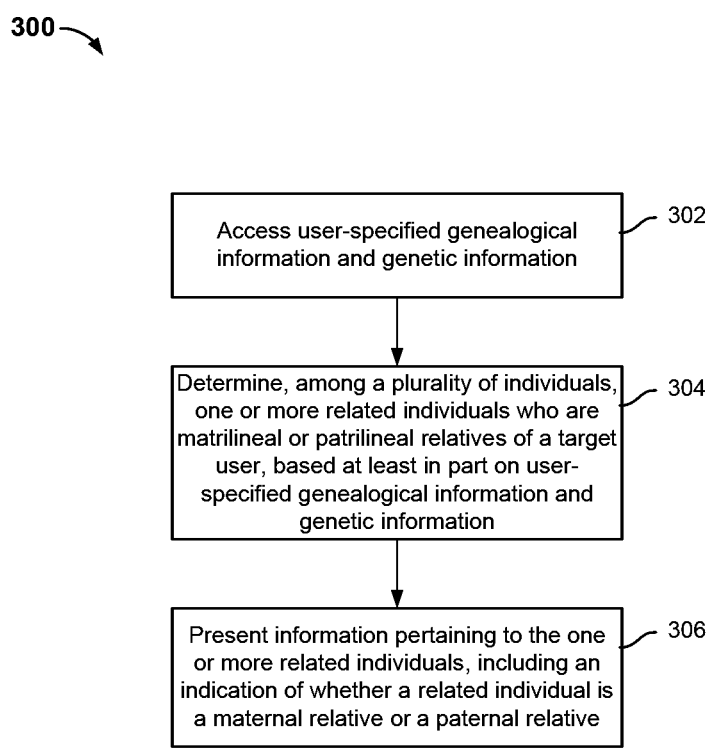
FIG. 3 is a flowchart illustrating an embodiment of a process for determining relative relationships.

FIG. 3 is a flowchart illustrating an embodiment of a process for determining relative relationships. Process 300 can be performed on a system such as 100.

At 302, user-specified genealogical information and genetic information (specifically, genetic information of recombinable DNAs) of individuals is accessed. In some embodiments, a database such as 110 is accessed to obtain user-specified genealogical information (e.g., family tree data of users in the database) and genetic information (e.g., sequence or marker data of recombinable DNAs of users in the database).

At 304, one or more related individuals who are relatives of a target individual and information pertaining to the one or more related individuals is determined among the plurality of individuals. In some embodiments, the determination is based at least in part on the user-specified genealogical information of some individuals in the database, and the genetic information of recombinable DNAs of some individuals in the database. For example, based on the user-specified information about a target user's parents (e.g., the names or user identifiers of the parents), the genetic information of the target user's mother (or father) can be located in the database (e.g., using the names or user identifiers as search keys). The system can determine genetic relatives of the target user's mother (or father) using techniques such as IBD-based relative identification. Details of the IBD-based technique are described below. Any genetic relative of the mother is a matrilineal relative of the target user, and any genetic relative of the father is a patrilineal relative of the target user. Accordingly, the information pertaining to any individual identified as a relative through the target user's mother or father includes information about whether the relative is a matrilineal relative or a patrilineal relative.

At 306, information pertaining to one or more related individuals is presented. The information that is presented includes an indication of whether the relative is a matrilineal relative or a patrilineal relative of the target individual. Depending on implementation and context, the information/indication can be presented differently.

Figure 4A:
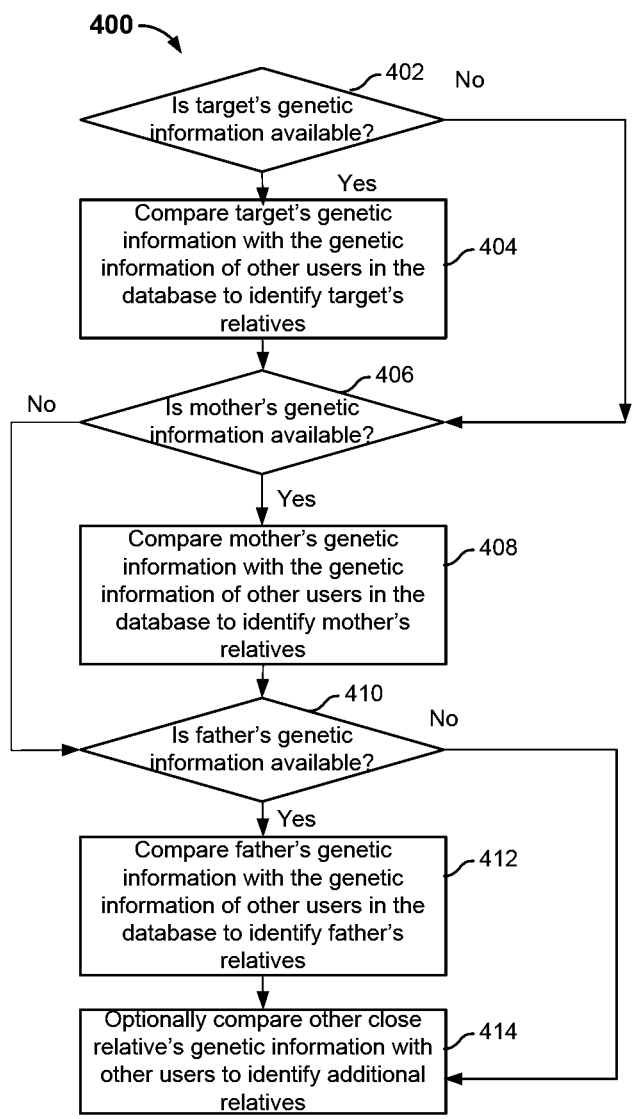
FIG. 4A is a flowchart illustrating an embodiment of a process for identifying matrilineal or patrilineal relatives of a target user.

FIG. 4A is a flowchart illustrating an embodiment of a process for identifying matrilineal or patrilineal relatives of a target user. Process 400 can be used to implement step 304 of process 300. Since a user is allowed to join the system without providing a DNA sample to be assayed, the user's genetic information may be unavailable. It is still possible to find matrilineal or patrilineal relatives in the database through genetic techniques, provided that the genetic information of one or more close relatives of the target user is available. Process 400 begins at 402, where it is determined whether the target user's genetic information is available. If so, at 404, the target user's genetic information is compared with the genetic information of other users in the database to identify relatives of the target user. In some embodiments, the target user's genetic information is compared with the genetic information of every other user in the database (except those already identified by the target as relatives) to determine if the two users are related. An example technique of how to determine if two users are related is described in connection with FIG. 11. If the user's genetic information is unavailable, control is transferred to 406.

At 406, it is determined whether the target user's mother's genetic information is available. If so, at 408, the mother's genetic information is compared with the genetic information of other users in the database to identify relatives of the mother. If the mother's genetic information is not available, control is transferred to 410.

At 410, it is determined whether the target user's father's genetic information is available. If so, at 412, the father's genetic information is compared with the genetic information of other users in the database to identify relatives of the father. If the father's genetic information is not available, control is transferred to 414. If 414 is not implemented, the process terminates.

At 414, other close relatives' genetic information, if available, is optionally compared with other users to identify additional relatives. For example, the genetic information of the target user's maternal (or paternal) aunts, uncles, grandmothers, and/or grandfathers can be compared with the genetic information of other users to identify additional matrilineal (or patrilineal) relatives.

The relative information is stored and can be presented to the target user. In some embodiments, when information about a relative is presented to the target user, information about how the relative is found (e.g., by comparing genetic information of the target user, the mother, or the father) is optionally presented.

Figure 4B:
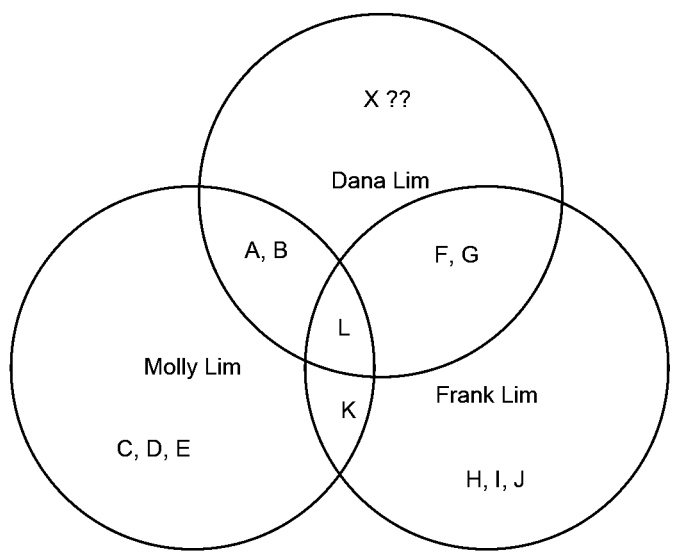
FIG. 4B is a Venn diagram illustrating an example in which matrilineal and patrilineal relatives are identified for a target user using process 400 of FIG. 4A.

FIG. 4B is a Venn diagram illustrating an example in which matrilineal and patrilineal relatives are identified for a target user using process 400 of FIG. 4A. In this example, target user Dana Lim has identified Molly Lim as her mother and Frank Lim as her father. The genetic information of all three users is available in the system. Through step 404 of process 400, it is determined that users A, B, F, G, L, and X are relatives of Dana. Through step 408, users A, B, C, D, E, L, and K are determined to be relatives of Molly. In some embodiments, for two users to be deemed to be relatives of each other, the amount of genetic information they share must reach a predetermined threshold. In this example, C, D, E, and K were found to be relatives of Molly but not Dana because while C, D, E, and K each share a sufficient amount of genetic information with Molly, the corresponding genes were not necessarily transmitted to Dana and there was not a sufficient match for C, D, E, and K to be deemed relatives of Dana during the initial process. However, since C, D, E, and K are relatives of Molly, they are also relatives (specifically maternal relatives) of Dana. An indicator associated with each of these users is set to indicate the matrilineal relationship with Dana. A special indicator associated with each of the users A, B, C, D, E, L, and K is set to indicate a matrilineal relationship with Dana. Similarly, through step 412, Frank's genetic information is compared with that of others in the database, and it is determined that users F, G, H, I, J, L, and K are relatives of Frank. Although H, I, and J, K are found to be relatives of Frank but not Dana, they are by definition relatives of Dana and are added to Dana's list of relatives. An indicator associated with each of these users is set to indicate the patrilineal relationship with Dana.

There are some special cases shown in this example. L is found to be relatives of Molly, Frank, and Dana. One possibility is that L is Dana's sibling. Another possibility is that there was intermarriage that caused branches of the family tree to merge (e.g., Molly's third cousin married Frank's third cousin, giving birth to a third cousin once removed, L). In any case, L and Dana share enough IBD regions that L is deemed to be Dana's relative as a result of the initial matching process. K is found to be relatives of both Molly and Frank but not of Dana. Again, it is possible that Molly's third cousin married Frank's third cousin, giving birth to a third cousin once removed, K. Further, K and Dana do not share sufficient IBD regions for K to be deemed a relative of Dana as a result of the initial matching process. Another special case shown in the example is X, who is someone found to be a relative of Dana but is a relative of neither Molly nor Frank. This is deemed an anomaly most likely attributed to an erroneous estimation of a match between Dana and X, between X and Molly, and/or between X and Frank.

Although in this example, it is assumed that Dana, Molly, and Frank have all been genotyped or sequenced, it is still possible to determine matrilineal/patrilineal relatives without requiring all three people to be genotyped or sequenced by making certain inferences. For example, if Dana is neither genotyped nor sequenced but Molly and Frank are, then the relatives of Molly (as determined by comparing Molly's genetic information with other users' genetic information) are inferred to be matrilineal relatives of Dana. Similarly, the relatives of Frank are inferred to be patrilineal relatives of Dana. Based on the example diagram shown in FIG. 4B, the only relative of Molly that is not identified with this method would be X, which is an anomaly. In another example, if Dana and Molly are genotyped/sequenced, but Frank is not, then any relative that is deemed a relative of Dana but not a relative of Molly can be inferred as patrilineal relatives of Dana. In the example diagram of FIGS. 4B, X, F, and G are deemed to be patrilineal relatives of Dana but H, I, and J remain unidentified.

The result of the relative finding process can be presented in many different ways. For example, a list view, a map view, and a surname view are described below. Other views are possible. Information about matrilineal relatives and patrilineal relatives can be presented separately (e.g., in different views) or together (e.g., in the same view but with indicators indicating the matrilineal/patrilineal status of the relative).

FIG. 5 is an example user interface screen of an embodiment of a list view interface displaying the relatives found in a process such as 300. In this example, relatives of Dana are sorted according to how closely related they are to Dana. An indicator shows whether each relative is a matrilineal or patrilineal relative. As shown, different icons are used to indicate different states, where matrilineal relatives are indicated using icon 502 and patrilineal relatives are indicated using icon 504. People similar to L, K, and X of FIG. 4 are indicated using icons 506, 508, and 510, respectively. Other visual representations of the data are possible in other embodiments. For example, the list can also be filtered according to matrilineal or patrilineal lines such that only matrilineal or patrilineal relatives are displayed. In some embodiments, information about how a relative is found (e.g., whether a relative is a genetic match of Dana and/or Molly only, of Dana and/or Frank only, of Dana, Molly, and Frank, of Molly and Frank only, or of Dana only) is optionally presented.

Figure 6:
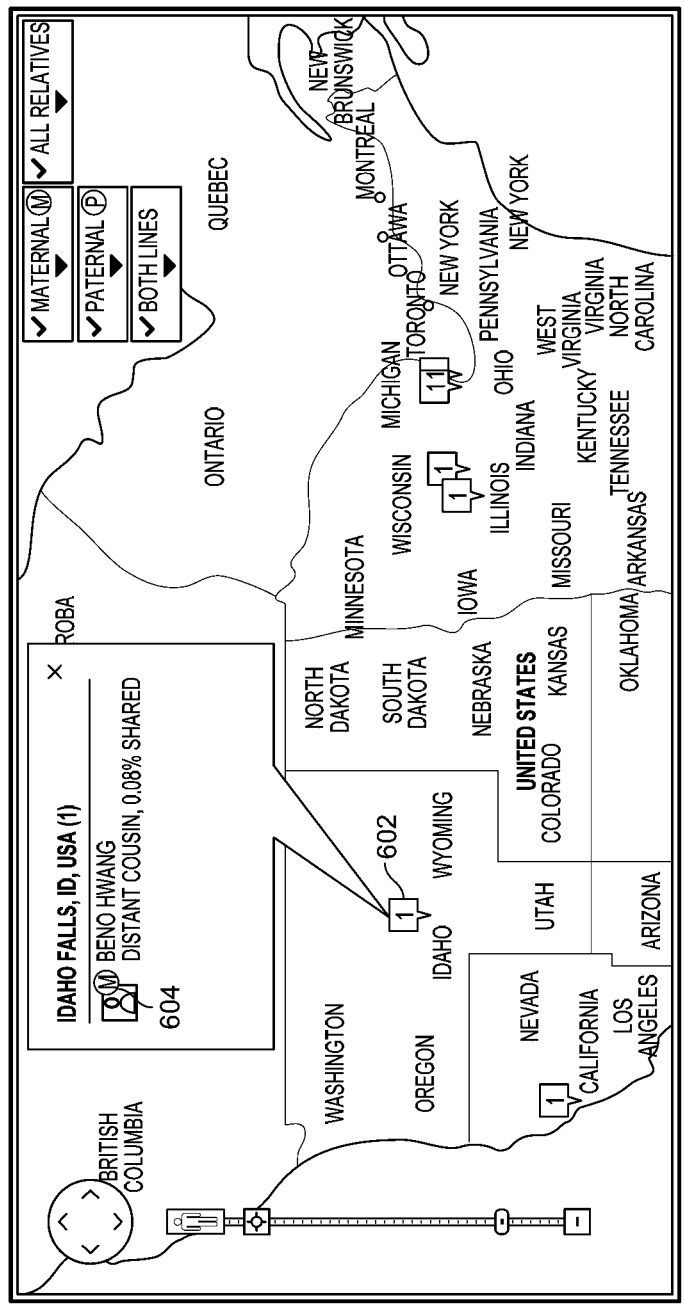
FIG. 6 is an example user interface screen of an embodiment of a map view interface displaying locations of the relatives found in a process such as 300.

FIG. 6 is an example user interface screen of an embodiment of a map view interface displaying locations of the relatives found in a process such as 300. In this example, family locations specified by the found relatives are geocoded and are displayed in an interactive map. In some embodiments, the interactive map is created using Google® Maps API. The user is given the option to select a location icon on the map, and view more details about the corresponding relative, including whether the relative is a matrilineal or patrilineal relative. For example, when location 602 is selected, a window is presented that displays information pertaining to the relative who specified this location as a part of his family locations information. A special badge 604 indicates that he is a matrilineal relative. In some embodiments, the user has the option to filter and view a selective type of location (e.g., to view birthplaces only, current residences only, etc.). In some embodiments, the user is also given the option to filter on the basis of matrilineal or patrilineal relatives and view the locations for only the matrilineal relatives or only the patrilineal relatives. This way, the user can get a better sense for where relatives on each side of the family are located (e.g., noticing that a large portion of the matrilineal relatives are from southern states and a large portion of the patrilineal relatives are from the western states, etc.).

Figure 7:
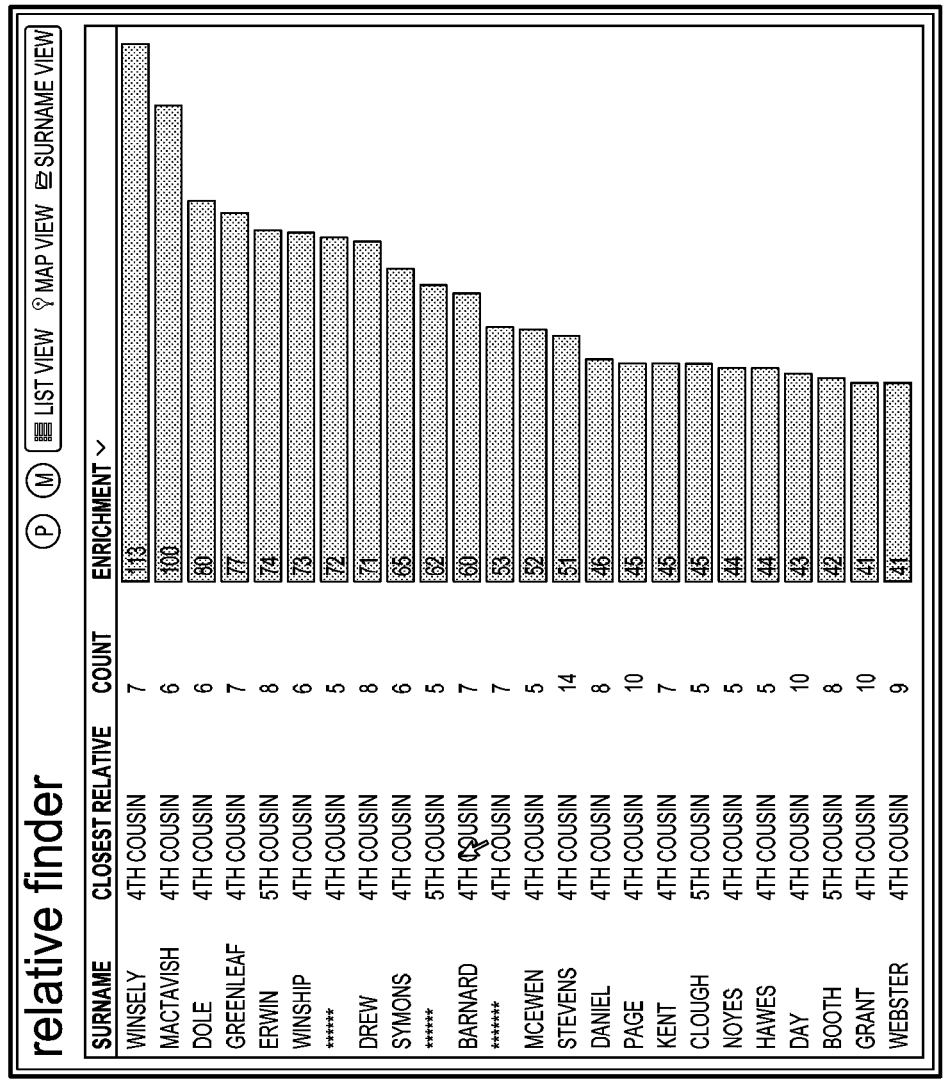
FIG. 7 is an example user interface of an embodiment of a surname view interface displaying the relatives found in a process such as 300.

FIG. 7 is an example user interface of an embodiment of a surname view interface displaying the relatives found in a process such as 300. As described above, each user is asked to provide family surnames when configuring her account profile. Thus, the surnames of the found relatives are sorted for presentation to the user. The ranking of a surname in the list depends on factors such as how frequently the surname appears in the family, and how unusual the surname is. How common a surname is in the general population can affect the how frequently a surname appears in the list of surnames associated with the relatives. A surname that is common in the general population (e.g., "Smith") can appear with high frequency in many family trees, but it does not mean that such a surname is overrepresented in any particular family. On the other hand, a surname that is uncommon in the general population but has a high frequency of appearance in one's family tree is overrepresented in this family. To account for this phenomenon, in some embodiments, the ranking of a surname depends in part on an enrichment value that measures the overrepresentation of the surname among family members. The enrichment value is low for common surnames and high for uncommon surnames. In some embodiments, the enrichment factor for a surname is computed by using a one-tailed binomial test, for which the inputs include a reference frequency and two counts, and the output includes a p-value. The frequency of the surname in the general population (according to census data or platform-wide data) is used as the reference frequency of the binomial test. The number of occurrences of the surname among the found relatives and the total number of surnames among the found relatives are used as counts in the binomial test to generate the p-value (p). For better usability, the enrichment factor is computed as $-\log 10(p)$. The higher the enrichment factor, the more unusual it is that the surname appears at a high frequency in the found relatives. In the example shown, although the surname "Stevens" appears at a higher frequency (14 counts) than the surname "Winsley" (7 counts), "Stevens" is more common in the general population and received a low enrichment value (51) than "Winsley" (113). "Winsley" therefore received a higher ranking than "Stevens."

In some embodiments, the surnames are displayed with an indicator indicating whether it appears more frequently on the mother's side or on the father's side. Alternatively, the user can filter names based on matrilineal or patrilineal association (e.g., by selecting an "M" button to display matrilineal surnames only or by selecting a "P" button to display patrilineal surnames only).

Figure 8:
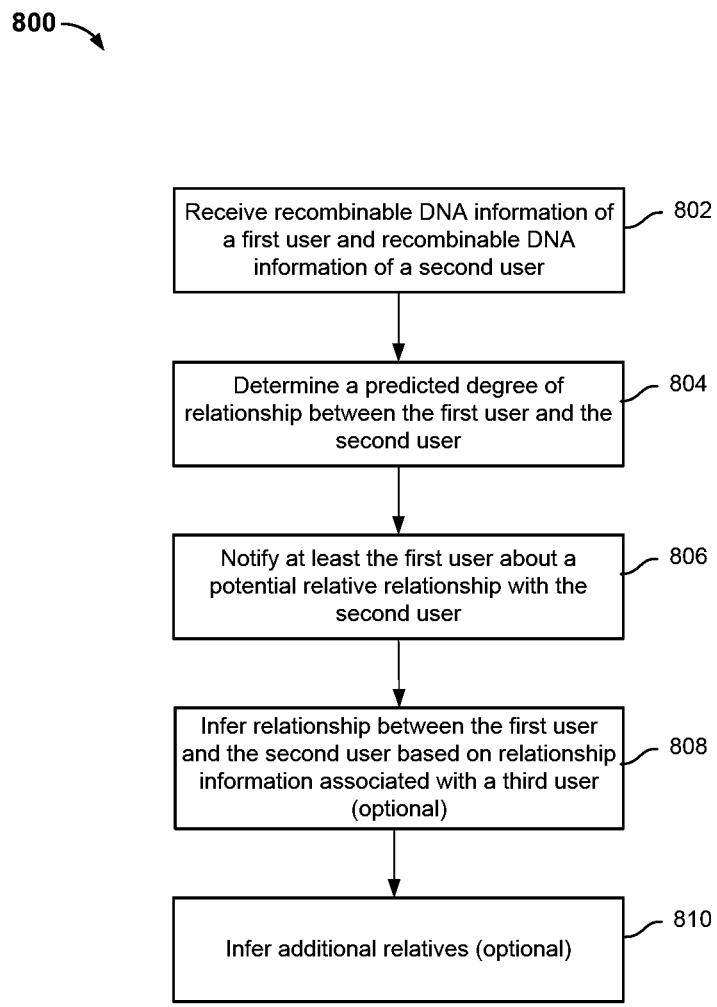
FIG. 8 is a flowchart illustrating an embodiment of a process of determining whether two users in the database are related.

FIG. 8 is a flowchart illustrating an embodiment of a process of determining whether two users in the database are related. Process 800 may be implemented on a relative finder system such as 100. The process may be invoked, for example, at a user's request to look for potential relatives this user may have in the database or by the system to assess the potential relationships among various users. At 802, recombinable DNA information of a first user (e.g., Dana) and of a second user (e.g., Bob) is received. In some embodiments, the information is retrieved from a database that stores recombinable DNA information of a plurality of users as well as any additional user information. For purposes of illustration, SNP information is described extensively in this and following examples. Other DNA information such as STR information and/or CNV information may be used in other embodiments.

At 804, a predicted degree of relationship between Dana and Bob is determined. In some embodiments, a range of possible relationships between the users is determined and a prediction of the most likely relationship between the users is made. In some embodiments, it is optionally determined whether the predicted degree of relationship at least meets a threshold. The threshold may be a user configurable value, a system default value, a value configured by the system's operator, or any other appropriate value. For example, Dana may select five generations as the maximum threshold, which means she is interested in discovering relatives with whom she shares a common ancestor five generations or closer. Alternatively, the system may set a default value minimum of three generations, allowing the users to by default find relatives sharing a common ancestor at least three generations out or beyond. In some embodiments, the system, the user, or both, have the option to set a minimum threshold (e.g., two generations) and a maximum threshold (e.g., six generations) so that the user would discover relatives within a maximum number of generations, but would not be surprised by the discovery of a close relative such as a sibling who was previously unknown to the user.

At 806, Dana or Bob (or both) is notified about her/his relative relationship with the other user. In some embodiments, the system actively notifies the users by sending messages or alerts about the relationship information when it becomes available. Other notification techniques are possible, for example by displaying a list or table of users that are found to be related to the user. Depending on system settings, the potential relatives may be shown anonymously for privacy protection, or shown with visible identities to facilitate making connections. In embodiments where a threshold is set, the user is only notified if the predicted degree of relationship at least meets the threshold. In some embodiments, a user is only notified if both of the user and the potential relative have "opted in" to receive the notification. In various embodiments, the user is notified about certain personal information of the potential relative, the predicted relationship, the possible range of relationships, the amount of DNA matching, or any other appropriate information.

In some embodiments, at 808, the process optionally infers additional relationships or refines estimates of existing relationships between the users based on other relative relationship information, such as the relative relationship information the users have with a third user. For example, although Dana and Bob are only estimated to be $6^{th}$ cousins after step 804, if among Dana's relatives in the system, a third cousin, Cathy, is also a sibling of Bob's, then Dana and Bob are deemed to be third cousins because of their relative relationships to Cathy. The relative relationships with the third user may be determined based on genetic information and analysis using a process similar to 800, based on non-genetic information such as family tree supplied by one of the users, or both.

In some embodiments, the relatives of the users in the system are optionally checked to infer additional relatives at 810. For example, if Bob is identified as a third cousin of Dana's, then Bob's relatives in the system (such as children, siblings, possibly some of the parents, aunts, uncles, cousins, etc.) are also deemed to be relatives of Dana's. In some embodiments a threshold is applied to limit the relationships within a certain range. Additional notifications about these relatives are optionally generated.

Process 800 can be repeated for other users in the system to identify additional relatives of Dana. Process 800 can also be repeated with respect to Molly and other users to identify Molly's relatives, as well as with respect to Frank and other users to identify Frank's relatives. The results can be organized according to the relatives and their relationships to Dana, Molly, and/or Frank, in a way that is similar to the Venn diagram of FIG. 4B. In other words, the relatives can be organized as matrilineal relatives only, patrilineal relatives only, matrilineal and patrilineal relatives, or neither matrilineal nor patrilineal relatives.

Figure 9:
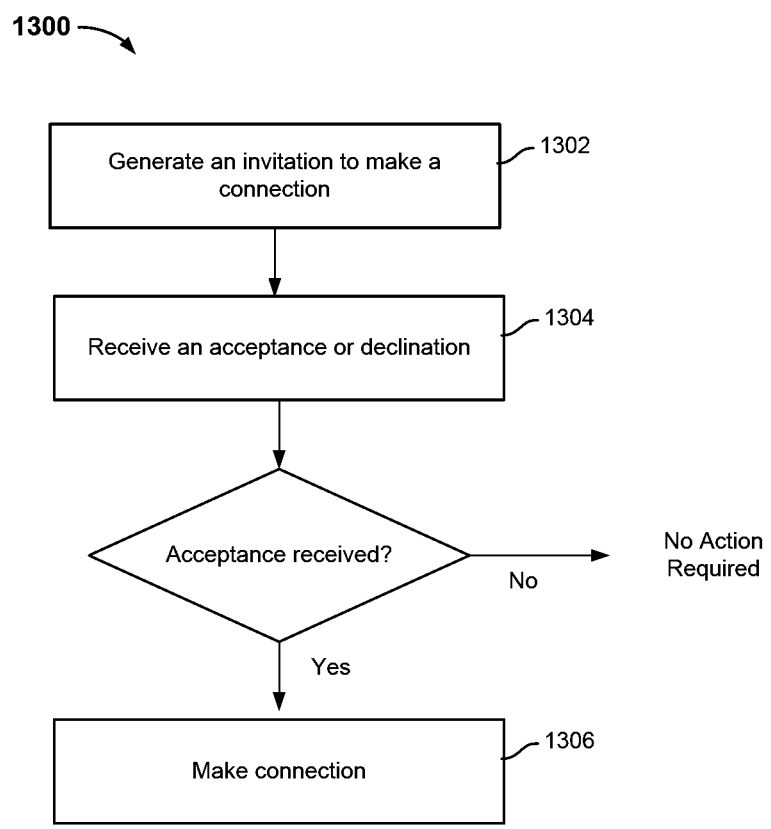
FIG. 9 is a flowchart illustrating an embodiment of a process for connecting a user with potential relatives found in the database.

Upon receiving a notification about another user who is a potential relative, the notified user is allowed to make certain choices about how to interact with the potential relative. FIG. 9 is a flowchart illustrating an embodiment of a process for connecting a user with potential relatives found in the database. The process may be implemented on a system 100, a relative finder system such as 102, a client device such as 106, or a combination thereof. In this example, it is assumed that it has been determined that Dana and Bob are possibly 4th cousins and that Dana has indicated that she would like to be notified about any potential relatives within 6 generations. In this example, process 1300 follows 806 of process 800, where a notification is sent to Dana, indicating that a potential relative has been identified. In some embodiments, the identity of Bob is disclosed to Dana. In some embodiments, the identity of Bob is not disclosed initially to protect Bob's privacy.

Upon receiving the notification, Dana decides that she would like to make a connection with the newly found relative. At 1302, an invitation from Dana to Bob inviting Bob to make a connection is generated. In various embodiments, the invitation includes information about how Dana and Bob may be related and any personal information Dana wishes to share such as her own ancestry information. Upon receiving the invitation, Bob can accept the invitation or decline. At 1304, an acceptance or a declination is received. If a declination is received, no further action is required. In some embodiments, Dana is notified that a declination has been received. If, however, an acceptance is received, at 1306, a connection is made between Dana and Bob. In various embodiments, once a connection is made, the identities and any other sharable personal information (e.g., genetic information, family history, phenotype/traits, etc.) of Dana and Bob are revealed to each other and they may interact with each other. In some embodiments, the connection information is updated in the database.

In some embodiments, a user can discover many potential relatives in the database at once. Additional potential relatives are added as more users join the system and make their genetic information available for the relative finding process. FIGS. 10A-10H are screenshots illustrating user interface examples in connection with process 1300.

Figures 10A, 10B:

FIG. 10A shows an interface example for the discovery view at the beginning of the process. No relative has been discovered at this point. In this example, a privacy feature is built into the relative finder application so that close relative information will only be displayed if both the user and the close relative have chosen to view close relatives. This is referred to as the "opt in" feature. The user is further presented with a selection button "show close relatives" to indicate that he/she is interested in finding out about close relatives. FIG. 10B shows a message that is displayed when the user selects "show close relatives." The message explains to the user how a close relative is defined. In this case, a close relative is defined as a first cousin or closer. In other words, the system has set a default minimum threshold of three degrees. The message further explains that unless there is already an existing connection between the user and the close relative, any newly discovered potential close relatives will not appear in the results unless the potential close relatives have also chosen to view their close relatives. The message further warns about the possibility of finding out about close relatives the user did not know he/she had. The user has the option to proceed with viewing close relatives or cancel the selection.

FIG. 10C shows the results in the discovery view. In this example, seven potential relatives are found in the database. The predicted relationship, the range of possible relationship, certain personal details a potential relative has made public, the amount of DNA a potential relative shares with the user, and the number of DNA segments the potential relative shares with the user are displayed. The user is presented with a "make contact" selection button for each potential relative.

The found relatives can be shown in a number of different views. Some examples are shown in FIGS. 5-7.

Figure 10D:
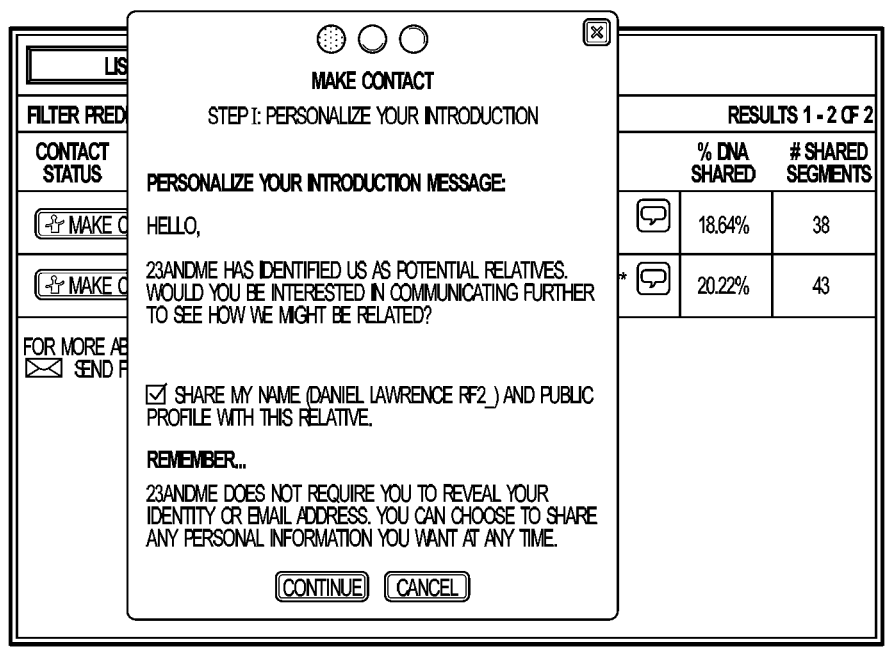
Figure 10E:
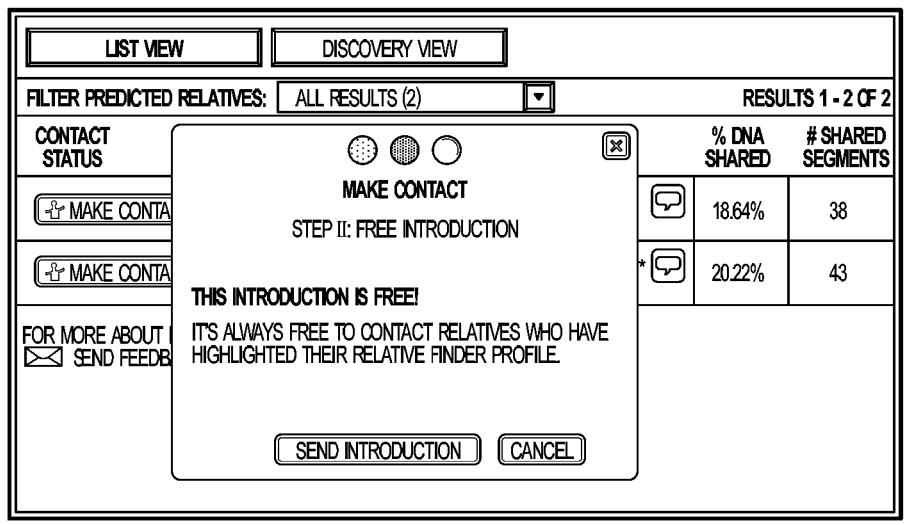
Figure 10F:
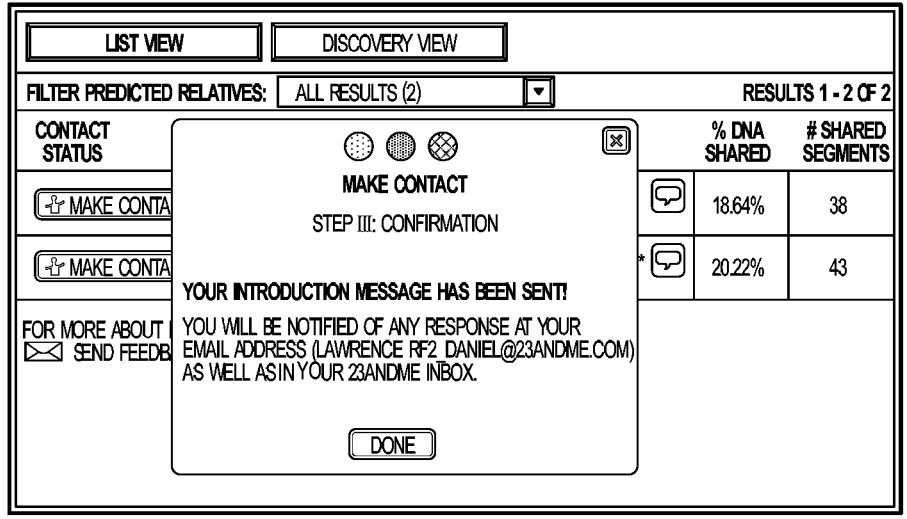

FIGS. 10D-10F show the user interface when the user selects to "make contact" with a potential relative. FIG. 10D shows the first step in making contact, where the user personalizes the introduction message and determines what information the user is willing to share with the potential relative. FIG. 10E shows an optional step in making contact, where the user is told about the cost of using the introduction service. In this case, the introduction is free. FIG. 10F shows the final step, where the introduction message is sent.

FIG. 10G shows the user interface shown to the potential relative upon receiving the introduction message. In this example, the discovery view indicates that a certain user/potential relative has requested to make a contact. The predicted relationship, personal details of the sender, and DNA sharing information are shown to the recipient. The recipient has the option to select "view message" to view the introduction message from the sender.

Figure 10H:

FIG. 10H shows the message as it is displayed to the recipient. In addition to the content of the message, the recipient is given the option to accept or decline the invitation to be in contact with the sender. If the recipient accepts the invitation, the recipient and the sender become connected and may view each other's information and/or interact with each other.

Many other user interfaces can be used in addition to or as alternatives of the ones shown above. For example, in some embodiments, at least some of the potential relatives are displayed in a family tree.

Determining the relationship between two users in the database is now described. In some embodiments, the determination includes comparing the DNA markers (e.g., SNPs) of two users and identifying IBD regions. The standard SNP-based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g., triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

Figure 11:
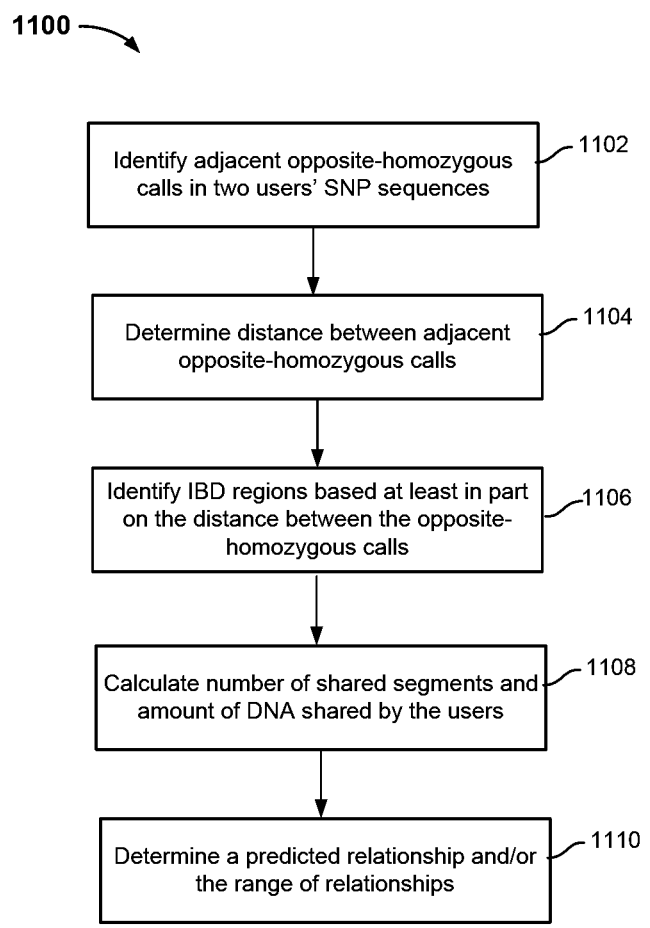
FIG. 11 is a diagram illustrating an embodiment of a process for determining the predicted degree of relationship between two users.

FIG. 11 is a diagram illustrating an embodiment of a process for determining the predicted degree of relationship between two users. Process 1100 may be implemented on a relative finder system such as 102 and is applicable to unphased data. At 1102, consecutive opposite-homozygous calls in the users' SNPs are identified. The consecutive opposite-homozygous calls can be identified by serially comparing individual SNPs in the users' SNP sequences or in parallel using bitwise operations as described below. At 1104, the distance between consecutive opposite-homozygous calls is determined. At 1106, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite homozygous calls is just below the 10 cM threshold. If a large enough number of genotype calls within that interval match exactly, the interval is deemed IBD.

Figure 12:
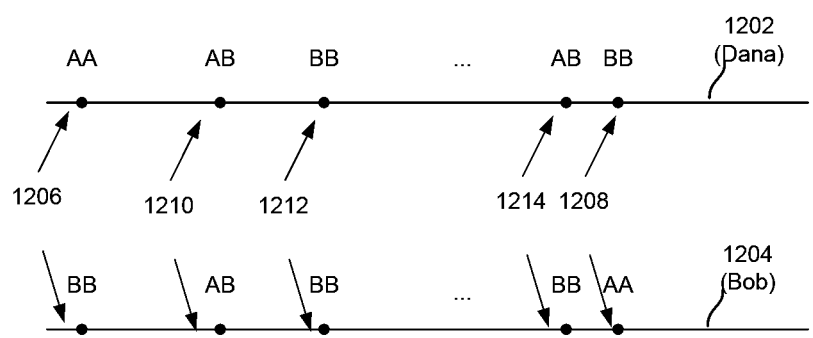
FIG. 12 is a diagram illustrating example DNA data used for IBD identification by process 1100.

FIG. 12 is a diagram illustrating example DNA data used for IBD identification by process 1100. 1202 and 1204 correspond to the SNP sequences of Dana and Bob, respectively. At location 1206, the alleles of Dana and Bob are opposite-homozygotes, suggesting that the SNP at this location resides in a non-IBD region. Similarly, at location 1208, the opposite-homozygotes suggest a non-IBD region. At location 1210, however, both pairs of alleles are heterozygotes, suggesting that there is potential for IBD. Similarly, there is potential for IBD at location 1212, where both pairs of alleles are identical homozygotes, and at location 1214, where Dana's pair of alleles is heterozygous and Bob's is homozygous. If there is no other opposite-homozygote between 1206 and 1208 and there are a large number of compatible calls between the two locations, it is then likely that the region between 1206 and 1208 is an IBD region.

Returning to FIG. 11, at 1108, the number of shared IBD segments and the amount of DNA shared by the two users are computed based on the IBD. In some embodiments, the longest IBD segment is also determined. In some embodiments, the amount of DNA shared includes the sum of the lengths of IBD regions and/or percentage of DNA shared. The sum is referred to as $IBD_{half}$ or half IBD because the individuals share DNA identical by descent for at least one of the homologous chromosomes. At 1110, the predicted relationship between the users, the range of possible relationships, or both, is determined using the $IBD_{half}$ and number of segments, based on the distribution pattern of $IBD_{half}$ and shared segments for different types of relationships. For example, in a first degree parent/child relationship, the individuals have $IBD_{half}$ that is 100% the total length of all the autosomal chromosomes and 22 shared autosomal chromosome segments; in a second degree grandparent/grandchild relationship, the individuals have $IBD_{half}$ that is approximately half the total length of all the autosomal chromosomes and many more shared segments; in each subsequent degree of relationship, the percentage of $IBD_{half}$ of the total length is about 50% of the previous degree. Also, for more distant relationships, in each subsequent degree of relationship, the number of shared segments is approximately half of the previous number.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

Figure 13:
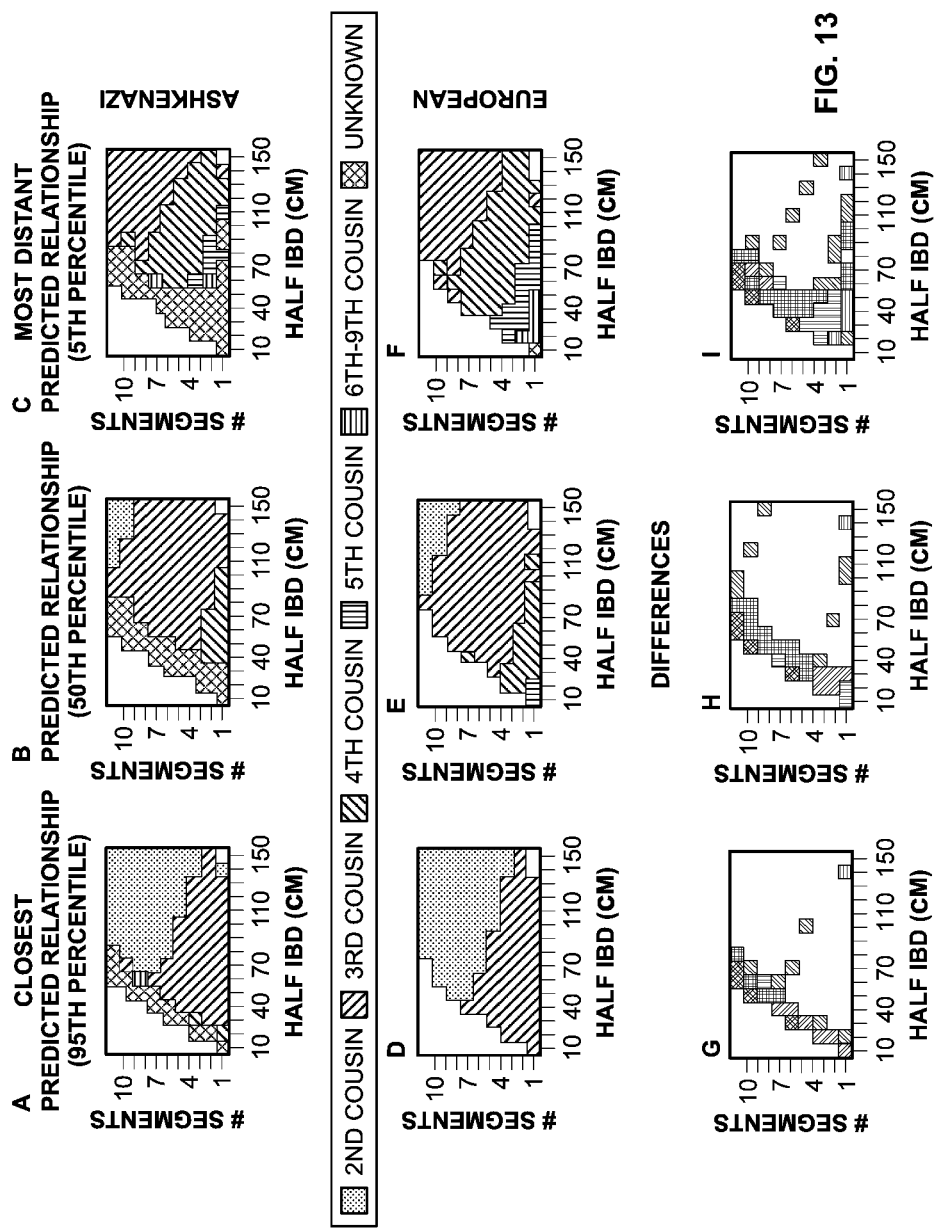
FIG. 13 shows the simulated relationship distribution patterns for different population groups according to one embodiment.

There is a statistical range of possible relationships for the same $IBD_{half}$ and shared segment number. In some embodiments, the distribution patterns are determined empirically based on survey of real populations. Different population groups may exhibit different distribution patterns. For example, the level of homozygosity within endogamous populations is found to be higher than in populations receiving gene flow from other groups. In some embodiments, the bounds of particular relationships are estimated using simulations of IBD using generated family trees. Based at least in part on the distribution patterns, the $IBD_{half}$, and shared number of segments, the degree of relationship between two individuals can be estimated. FIG. 13 shows the simulated relationship distribution patterns for different population groups according to one embodiment. In particular, Ashkenazi Jews and Europeans are two population groups surveyed. In panels A-C, for each combination of $IBD_{half}$ and the number of IBD segments in an Ashkenazi sample group, the 95%, 50% and 5% of obtained nth degree cousinships from 1 million simulated pedigrees are plotted. In panels D-F, for each combination of $IBD_{half}$ and the number of IBD segments in a European sample group, the 95%, 50% and 5% of obtained nth degree cousinships from 1 million simulated pedigrees are plotted. In panels G-I, the differences between Ashkenazi and European distant cousinship for the prior panels are represented. Each nth cousinship category is scaled by the expected number of nth degree cousins given a model of population growth. Simulations are conducted by specifying an extended pedigree and creating simulated genomes for the pedigree by simulating the mating of individuals drawn from a pool of empirical genomes. Pairs of individuals who appear to share $IBD_{half}$ that was not inherited through the specified simulated pedigree are marked as "unknown" in panels A-F. Thus, special distribution patterns can be used to find relatives of users who have indicated that they belong to certain distinctive population groups such as the Ashkenazi.

The amount of IBD sharing is used in some embodiments to identify different population groups. For example, for a given degree of relationship, since Ashkenazi tend to have much more IBD sharing than non-Ashkenazi Europeans, users may be classified as either Ashkenazi or non-Ashkenazi Europeans based on the number and pattern of IBD matches.

In some embodiments, instead of, or in addition to, determining the relationship based on the overall number of IBD segments and percent DNA shared, individual chromosomes are examined to determine the relationship. For example, X chromosome information is received in some embodiments in addition to the autosomal chromosomes. The X chromosomes of the users are also processed to identify IBD. Since one of the X chromosomes in a female user is passed on from her father without recombination, the female inherits one X chromosome from her paternal grandmother and another one from her mother. Thus, the X chromosome undergoes recombination at a slower rate compared to autosomal chromosomes and more distant relationships can be predicted using IBD found on the X chromosomes.

In some embodiments, analyses of mutations within IBD segments can be used to estimate ages of the IBD segments and refine estimates of relationships between users.

In some embodiments, the relationship determined is verified using non-DNA information. For example, the relationship may be checked against the users' family tree information, birth records, or other user information.

Figure 14:
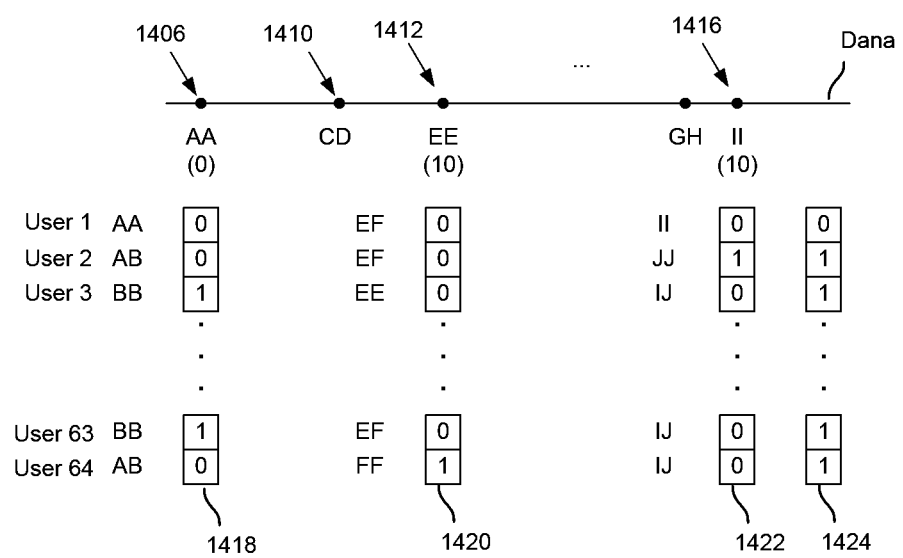
FIG. 14 is a diagram illustrating an embodiment of a highly parallel IBD identification process.

In some embodiments, the efficiency of IBD region identification is improved by comparing a user's DNA information with the DNA information of multiple other users in parallel and using bitwise operations. FIG. 14 is a diagram illustrating an embodiment of a highly parallel IBD identification process. Dana's SNP calls are compared with those of multiple other users. Dana's SNP calls are pre-processed to identify ones that are homozygous. Dana's heterozygous calls are not further processed since they always indicate that there is a possibility of IBD with another user. For each SNP call in Dana's genome that is homozygous, the zygosity states in the corresponding SNP calls in the other users are encoded. In this example, compatible calls (e.g., heterozygous calls and same homozygous calls) are encoded as 0 and opposite-homozygous calls are encoded as 1. For example, for homozygous SNP call AA at location 1406, opposite-homozygous calls BB are encoded as 1 and compatible calls (AA and AB) are encoded as 0; for homozygous SNP call EE at location 1412, opposite-homozygous calls FF are encoded as 1 and compatible calls (EE and EF) are encoded as 0, etc. The encoded representations are stored in arrays such as 1418, 1420, and 1422. In some embodiments, the length of the array is the same as the word length of the processor to achieve greater processing efficiency. For example, in a 64-bit processing system, the array length is set to 64 and the zygosity of 64 users' SNP calls are encoded and stored in the array.

A bitwise operation is performed on the encoded arrays to determine whether a section of DNA such as the section between locations 1406 and 1410 includes opposite-homozygous calls. In this example, a bitwise OR operation is performed to generate a result array 1424. Any user with no opposite-homozygous calls between beginning location 1406 and ending location 1416 results in an entry value of 0 in array 1424. The corresponding DNA segment, therefore, is deemed as an IBD region for such user and Dana. In contrast, users with opposite-homozygotes result in corresponding entry values of 1 in array 1424 and they are deemed not to share IBD with Dana in this region. In the example shown, user 1 shares IBD with Dana while other users do not.

In some embodiments, phased data is used instead of unphased data. These data can come directly from assays that produce phased data, or from statistical processing of unphased data. IBD regions are determined by matching the SNP sequences between users. In some embodiments, sequences of SNPs are stored in dictionaries using a hashtable data structure for the ease of comparison. FIG. 15 is a diagram illustrating an example in which phased data is compared to identify IBD. The sequences are split along predefined intervals into non-overlapping words. Other embodiments may use overlapping words. Although a preset length of 3 is used for purposes of illustration in the example shown, many implementations may use words of longer lengths (e.g., 100). Also, the length does not have to be the same for every location. In FIG. 15, in Dana's chromosome pair 1, chromosome 1502 is represented by words AGT, CTG, CAA, . . . and chromosome 1504 is represented by CGA, CAG, TCA, . . . . At each location, the words are stored in a hash table that includes information about a plurality of users to enable constant retrieval of which users carry matching haplotypes. Similar hash tables are constructed for other sequences starting at other locations. To determine whether Bob's chromosome pair 1 shares any IBD with Dana's, Bob's sequences are processed into words at the same locations as Dana's. Thus, Bob's chromosome 1506 yields CAT, GAC, CCG, . . . and chromosome 1508 yields AAT, CTG, CAA, . . . . Every word from Bob's chromosomes is then looked up in the corresponding hash table to check whether any other users have the same word at that location in their genomes. In the example shown, the second and third words of chromosome 1508 match second and third words of Dana's chromosome 1502. This indicates that SNP sequence CTGCAA is present in both chromosomes and suggests the possibility of IBD sharing. If enough matching words are present in close proximity to each other, the region would be deemed IBD.

In some embodiments, relative relationships found using the techniques described above are used to infer characteristics about the users that are related to each other. In some embodiments, the inferred characteristic is based on non-genetic information pertaining to the related users. For example, if a user is found to have a number of relatives that belong to a particular population group, then an inference is made that the user may also belong to the same population group. In some embodiments, genetic information is used to infer characteristics, in particular characteristics specific to shared IBD segments of the related users. Assume, for example, that Dana has sequenced her entire genome but her relatives in the system have only genotyped SNP data. If Dana's genome sequence indicates that she may have inherited a disease gene, then, with Dana's permission, Dana's relatives who have shared IBD with Dana in the same region that includes the disease gene may be notified that they are at risk for the same disease.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for determining relative relationships among a plurality of individuals, comprising:
    one or more computer processors to:
        access user-specified genealogical information of at least some of the plurality of individuals and genetic information of recombinable deoxyribonucleic acids (DNAs) of at least some of the plurality of individuals;

determine, among the plurality of individuals, one or more related individuals who are relatives of a target individual, and information pertaining to the one or more related individuals, wherein:
    the determination is based at least in part on the user-specified genealogical information of at least some of the plurality of individuals, and the genetic information of recombinable DNAs of at least some of the plurality of individuals; and
    the information pertaining to the one or more related individuals includes whether a related individual is a matrilineal relative or a patrilineal relative of the target individual;
present information pertaining to at least one of the one or more related individuals, including to present an indication of whether the at least one of the one or more related individuals is a matrilineal relative or a patrilineal relative of the target individual;
present an option to filter the determined one or more related individuals on the basis of matrilineal relatives or patrilineal relatives;
receive a user selection associated with the option; and
display only matrilineal relatives or only patrilineal relatives among the determined one or more related individuals based on the user selection; and
one or more memories coupled to the one or more processors, configured to provide the one or more processors with instructions.

2. The system of claim 1, wherein the one or more processors are further to obtain at least a portion of the user-specified genealogical information from the target individual.

3. The system of claim 1, wherein the genetic information includes genotype information.

4. The system of claim 1, wherein to determine one or more related individuals who are relatives of the target individual includes:
to access information pertaining to a specified relative who is specified as a matrilineal relative or a patrilineal relative of the target individual; and
to identify, among the plurality of individuals, one or more individuals whose genetic information matches genetic information of the specified relative of the target individual.

5. The system of claim 4, wherein to present information pertaining to at least one of the one or more related individuals further includes to present an indication that the at least one of the one or more related individuals is identified based at least in part on matching genetic information with respect to the specified relative.

6. The system of claim 1, wherein information pertaining to a plurality of the one or more related individuals is presented.

7. The system of claim 6, wherein to present information pertaining to the plurality of related individuals further includes to separately present information pertaining to those individuals identified as matrilineal relatives and information pertaining to those individuals identified as patrilineal relatives.

8. The system of claim 6, wherein to present information pertaining to the plurality of related individuals includes to present the information to be displayed in a list view.

9. The system of claim 6, wherein the information pertaining to the plurality of related individuals includes geographical location information.

10. The system of claim 9, wherein to present information pertaining to the plurality of related individuals further includes to present the information to be displayed in a map view illustrating the geographical location information.

11. The system of claim 1, wherein the information pertaining to at least one of the one or more related individuals includes surnames of the related individuals.

12. The system of claim 11, wherein to present information pertaining to at least one of the one or more related individuals further includes to sort the surname information, and to display surnames according to patrilineal association or matrilineal association.

13. The system of claim 1, wherein to determine one or more related individuals who are relatives of the target individual includes to compare genetic information of at least some of the plurality of individuals with a genotyped parent of the target individual to identify one or more Inheritance By Descent (IBD) regions.

14. The system of claim 1, wherein the one or more computer processors are further to cause a display interface to display a first type of graphical icon representing one or more matrilineal relatives among the one or more related individuals, and a second type of graphical icon representing one or more patrilineal relatives among the one or more related individuals, the first type of graphical icon being different from the second type of graphical icon.

15. A method of determining relative relationships among a plurality of individuals, comprising:
accessing user-specified genealogical information of at least some of the plurality of individuals and genetic information of recombinable deoxyribonucleic acids (DNAs) of at least some of the plurality of individuals;
determining, using one or more computer processors and among the plurality of individuals, one or more related individuals who are relatives of a target individual, and information pertaining to the one or more related individuals, wherein:
    the determination is based at least in part on the user-specified genealogical information of at least some of the plurality of individuals, and the genetic information of recombinable DNAs of at least some of the plurality of individuals; and
    the information pertaining to the one or more related individuals includes whether a related individual is a matrilineal relative or a patrilineal relative of the target individual; and
presenting information pertaining to at least one of the one or more related individuals, including to present an indication of whether the at least one of the one or more related individuals is a matrilineal relative or a patrilineal relative of the target individual;
presenting an option to filter the determined one or more related individuals on the basis of matrilineal relatives or patrilineal relatives;
receiving a user selection associated with the option; and
displaying only matrilineal relatives or only patrilineal relatives among the determined one or more related individuals based on the user selection.

16. The method of claim 15, further comprising obtaining at least a portion of the user-specified genealogical information from the target individual.

17. The method of claim 15, wherein the genetic information includes genotype information.

18. The method of claim 15, wherein determining one or more related individuals who are relatives of the target individual includes:
accessing information pertaining to a specified relative who is specified as a matrilineal relative or a patrilineal relative of the target individual; and identifying, among the plurality of individuals, one or more individuals whose genetic information matches genetic information of the specified relative of the target individual.

19. The method of claim 15, wherein information pertaining to a plurality of the one or more related individuals is presented.

20. The method of claim 15, wherein the information pertaining to at least one of the one or more related individuals includes surnames of the related individuals.

21. The method of claim 15, wherein to determine one or more related individuals who are relatives of the target individual includes to compare genetic information of at least some of the plurality of individuals with a genotyped parent of the target individual to identify one or more Inheritance By Descent (IBD) regions.

22. The method of claim 15, further comprising causing a display interface to display a first type of graphical icon representing one or more matrilineal relatives among the one or more related individuals, and a second type of graphical icon representing one or more patrilineal relatives among the one or more related individuals, the first type of graphical icon being different from the second type of graphical icon.

23. A computer program product for determining relative relationships among a plurality of individuals, the computer program product being embodied in a tangible computer readable storage medium and comprising computer instructions for:

accessing user-specified genealogical information of at least some of the plurality of individuals and genetic information of recombinable deoxyribonucleic acids (DNAs) of at least some of the plurality of individuals;

determining, among the plurality of individuals, one or more related individuals who are relatives of a target individual, and information pertaining to the one or more related individuals, wherein:

the determination is based at least in part on the user-specified genealogical information of at least some of the plurality of individuals, and the genetic information of recombinable DNAs of at least some of the plurality of individuals; and the information pertaining to the one or more related individuals includes whether a related individual is a matrilineal relative or a patrilineal relative of the target individual;

presenting information pertaining to at least one of the one or more related individuals, including to present an indication of whether the at least one of the one or more related individuals is a matrilineal relative or a patrilineal relative of the target individual;

presenting an option to filter the determined one or more related individuals on the basis of matrilineal relatives or patrilineal relatives;

receiving a user selection associated with the option; and displaying only matrilineal relatives or only patrilineal relatives among the determined one or more related individuals based on the user selection.

* * * * *